(12) United States Patent
Issayeva et al.

(10) Patent No.: US 11,789,583 B2
(45) Date of Patent: *Oct. 17, 2023

(54) METHOD AND APPARATUS FOR A THREE DIMENSIONAL INTERFACE

(71) Applicant: WEST TEXAS TECHNOLOGY PARTNERS, LLC, Waco, TX (US)

(72) Inventors: Iryna Issayeva, Foster City, CA (US); Sleiman Itani, East Palo Alto, CA (US); Allen Yang Yang, Richmond, CA (US); Mohamed Nabil Hajj Chehade, Los Angeles, CA (US)

(73) Assignee: West Texas Technology Partners, LLC

( * ) Notice: Subject to any disclaimer, the term of this patent is extended or adjusted under 35 U.S.C. 154(b) by 0 days.

This patent is subject to a terminal disclaimer.

(21) Appl. No.: 17/001,649

(22) Filed: Aug. 24, 2020

(65) Prior Publication Data

US 2020/0387290 A1  Dec. 10, 2020

Related U.S. Application Data

(63) Continuation of application No. 16/271,020, filed on Feb. 8, 2019, now Pat. No. 10,782,848, which is a
(Continued)

(51) Int. Cl.
*G06F 3/01* (2006.01)
*G06F 3/04815* (2022.01)
(Continued)

(52) U.S. Cl.
CPC .......... *G06F 3/04815* (2013.01); *A61B 34/20* (2016.02); *A61B 34/25* (2016.02);
(Continued)

(58) Field of Classification Search
CPC ................. G06F 3/011; G06F 3/04815; G06F 2203/04802; G06F 3/017; G06F 3/0346;
(Continued)

(56) References Cited

U.S. PATENT DOCUMENTS 6,222,465 B1    4/2001  Kumar et al.
6,243,054 B1*   6/2001  DeLuca ............... H04N 13/279
                                              348/E13.058
(Continued)

*Primary Examiner* — Dismery Mercedes
(74) *Attorney, Agent, or Firm* — Cadwalader, Wickersham & Taft LLP

(57) ABSTRACT

A method, system, apparatus, and/or device for interacting with a three dimensional interface. The method, system, apparatus, and/or device may include: generating a zone associated with a virtual object, wherein the zone includes a first space approximate to at least a portion of the object that is distinct from a second space occupied by the object; determine an uncertainty level of a sensor to identify an input in the zone; in response to the uncertainty level exceeding a first level, increasing a size of the zone, wherein the increased size of the zone increases a precision level of the sensor; and in response to the uncertainty level being below a second level, decreasing the size of the zone, wherein the decreased size of the zone decreases the precision level of the sensor.

18 Claims, 11 Drawing Sheets

Related U.S. Application Data continuation of application No. 13/797,715, filed on Mar. 12, 2013, now Pat. No. 10,241,638.

(60) Provisional application No. 61/721,948, filed on Nov. 2, 2012.

(51) Int. Cl.

| | | |
|---|---|---|
| *G06F 3/03* | (2006.01) | |
| *G06T 15/00* | (2011.01) | |
| *G06F 3/0346* | (2013.01) | |
| *G06F 3/0481* | (2022.01) | |
| *G02B 27/01* | (2006.01) | |
| *G06F 3/038* | (2013.01) | |
| *G06F 3/04842* | (2022.01) | |
| *A61B 34/20* | (2016.01) | |
| *G06T 19/20* | (2011.01) | |
| *G03H 1/08* | (2006.01) | |
| *A61B 34/00* | (2016.01) | |
| *H04N 13/388* | (2018.01) | |
| *G03H 1/02* | (2006.01) | |
| *G06F 3/04845* | (2022.01) | |
| *A61B 90/00* | (2016.01) | |

(52) U.S. Cl.
CPC ......... *G02B 27/017* (2013.01); *G03H 1/0248* (2013.01); *G03H 1/08* (2013.01); *G06F 3/011* (2013.01); *G06F 3/0346* (2013.01); *G06F 3/0383* (2013.01); *G06F 3/0481* (2013.01); *G06F 3/04842* (2013.01); *G06F 3/04845* (2013.01); *G06T 19/20* (2013.01); *H04N 13/388* (2018.05); *A61B 2090/365* (2016.02); *G02B 2027/014* (2013.01); *G02B 2027/0134* (2013.01); *G02B 2027/0187* (2013.01); *G06F 2203/04802* (2013.01); *G06F 2203/04805* (2013.01)

(58) Field of Classification Search
CPC .. G06F 3/0304; G06F 3/04842; G06F 3/0482; G06F 3/0481; G06F 3/038; G06F 3/03545; G06F 3/0484; G06F 3/0416; G06F 3/033; G06T 19/006; G06T 19/003; G06T 13/20; G06T 15/00; G06T 15/08; G06T 17/00; G06T 2207/10012; G06T 19/00; G06T 19/20; G06T 2200/04; G02B 27/017; G02B 27/0075; G02B 2027/014; G02B 2027/0134; G06K 9/6261; G06K 9/00671; G06K 9/3233; A61B 34/10; A61B 34/25; A61B 34/76; A61B 5/1122; A61B 5/1127; A61B 2090/365; G03H 1/08

See application file for complete search history.

(56) References Cited

U.S. PATENT DOCUMENTS

| | | | |
|---|---|---|---|
| 6,618,047 B1 | 9/2003 | Lim | |
| 6,798,412 B2 | 9/2004 | Cowperthwaite | |
| 7,227,526 B2 | 6/2007 | Hildreth | |
| 7,292,240 B2 | 11/2007 | Okuno et al. | |
| 7,493,153 B2 * | 2/2009 | Ahmed | G02B 27/017 600/407 |
| 7,626,571 B2 | 12/2009 | Conti et al. | |
| 7,743,348 B2 | 6/2010 | Robbins et al. | |
| 7,746,321 B2 * | 6/2010 | Banning | G03B 21/006 345/157 |
| 7,880,726 B2 | 2/2011 | Nakadaira et al. | |
| 8,334,867 B1 * | 12/2012 | Davidson | G06F 3/04845 715/848 |
| 8,451,220 B2 | 5/2013 | El Dokor | |
| 8,458,225 B2 | 6/2013 | Salemann | |
| 8,465,668 B2 | 6/2013 | Bittner et al. | |
| 8,477,139 B2 | 7/2013 | Robinet et al. | |
| 8,659,658 B2 | 2/2014 | Vassigh et al. | |
| 8,681,178 B1 * | 3/2014 | Tseng | G06T 19/006 345/629 |
| 8,810,600 B2 | 8/2014 | Bohn et al. | |
| 8,819,591 B2 | 8/2014 | Wang et al. | |
| 8,836,768 B1 | 9/2014 | Rafii et al. | |
| 8,933,876 B2 | 1/2015 | Galor et al. | |
| 8,933,912 B2 | 1/2015 | Ambrus et al. | |
| 8,963,834 B2 | 2/2015 | Park et al. | |
| 9,063,649 B2 | 6/2015 | Kim | |
| 9,292,184 B2 * | 3/2016 | Hosenpud | G06F 3/04815 |
| 9,495,068 B2 | 11/2016 | Morishita et al. | |
| 10,013,138 B2 | 7/2018 | Itani | |
| 10,163,264 B2 | 12/2018 | Abercrombie et al. | |
| 10,241,638 B2 * | 3/2019 | Issayeva | G06F 3/011 |
| 10,423,296 B2 | 9/2019 | Yang et al. | |
| 10,782,848 B2 * | 9/2020 | Issayeva | G06F 3/04815 |
| 2002/0041327 A1 * | 4/2002 | Hildreth | G06F 3/017 348/E13.016 |
| 2002/0064382 A1 * | 5/2002 | Hildreth | G06T 7/254 348/169 |
| 2003/0142068 A1 * | 7/2003 | DeLuca | G06V 40/20 348/E13.058 |
| 2004/0010346 A1 | 1/2004 | Stewart et al. | |
| 2004/0233222 A1 | 11/2004 | Lee et al. | |
| 2005/0174361 A1 * | 8/2005 | Kobayashi | G06F 3/012 345/633 |
| 2006/0098873 A1 | 5/2006 | Hildreth et al. | |
| 2007/0176899 A1 * | 8/2007 | Yoo | G06F 3/03542 345/158 |
| 2008/0018595 A1 | 1/2008 | Hildreth et al. | |
| 2008/0059578 A1 * | 3/2008 | Albertson | G06F 3/016 352/85 |
| 2008/0118595 A1 | 5/2008 | Hawkes | |
| 2008/0204404 A1 * | 8/2008 | Kneissler | H04N 21/42222 348/E7.087 |
| 2009/0077504 A1 | 3/2009 | Bell et al. | |
| 2009/0183125 A1 | 7/2009 | Magal et al. | |
| 2010/0110384 A1 | 5/2010 | Maekawa | |
| 2010/0253679 A1 | 10/2010 | Vyakhirev | |
| 2011/0107270 A1 * | 5/2011 | Wang | G16H 20/40 703/11 |
| 2011/0128555 A1 * | 6/2011 | Rotschild | G03H 1/0005 359/9 |
| 2011/0149042 A1 | 6/2011 | Lee et al. | |
| 2011/0169832 A1 * | 7/2011 | Brown | G06F 3/011 345/427 |
| 2011/0191707 A1 | 8/2011 | Lee et al. | |
| 2011/0193939 A1 * | 8/2011 | Vassigh | G06F 3/011 348/169 |
| 2011/0202553 A1 * | 8/2011 | Salemann | G06F 3/04815 707/769 |
| 2011/0216090 A1 | 9/2011 | Woo et al. | |
| 2011/0279364 A1 * | 11/2011 | Koshiyama | G06F 3/0443 345/156 |
| 2012/0052917 A1 * | 3/2012 | Kim | G06F 3/04883 455/566 |
| 2012/0117514 A1 | 5/2012 | Kim et al. | |
| 2012/0229381 A1 | 9/2012 | Landridge | |
| 2013/0095924 A1 * | 4/2013 | Geisner | A63F 13/21 463/32 |
| 2013/0194396 A1 | 8/2013 | Sonobe | |
| 2013/0257692 A1 | 10/2013 | Yang et al. | |
| 2014/0104274 A1 | 4/2014 | Hilliges et al. | |
| 2014/0115520 A1 | 4/2014 | Itani | |
| 2014/0181755 A1 * | 6/2014 | Oh | G06F 3/005 715/848 |
| 2014/0347329 A1 * | 11/2014 | Ware | G06F 3/04815 345/179 |
| 2015/0020031 A1 | 1/2015 | El Dokor et al. | |

* cited by examiner

METHOD AND APPARATUS FOR A THREE DIMENSIONAL INTERFACE

CROSS-REFERENCE TO RELATED APPLICATION

This application is a continuation of U.S. patent application Ser. No. 16/271,020, filed Feb. 8, 2019, which claims priority to U.S. patent application Ser. No. 13/797,715, filed Mar. 12, 2013, which claims priority to benefit of U.S. Provisional Application Ser. No. 61/721,948, filed on Nov. 2, 2012, which are hereby incorporated by reference for all purposes.

FIELD OF THE INVENTION

This invention relates to three dimensional interfaces. More particularly, this invention relates to approaches for user interaction with three dimensional interfaces, and the behavior of three dimensional interfaces responsive to user actions.

DESCRIPTION OF RELATED ART

Generally speaking, a user interface is the space or environment wherein a user interacts with some system. The term is frequently applied to the use of computers and other information systems.

To date, many user interfaces have been designed to support interaction in two dimensions. This approach can be functional for a user interface in a two dimensional environment, such as a flat display screen. However, two dimensional interfaces can be problematic for systems that operate in more than two dimensions, e.g. three dimensional interfaces.

There is a need for a simple, efficient method and apparatus for interacting with a three dimensional interface.

BRIEF SUMMARY OF THE INVENTION

The present invention contemplates a variety of systems, apparatus, methods, and paradigms for interacting with a three dimensional interface.

In one embodiment of the present invention, a method is provided that includes generating, in a processor, a three dimensional interface and at least one virtual object in the interface. The method further includes defining an interaction zone associated with the virtual object, generating the interaction zone in the interface, and defining a stimulus of the interaction zone and a response to the stimulus. When the stimulus is sensed, the response is executed.

The interface may be outputted as a stereo interface, and/or may be outputted on a head mounted display. The interface may be transparent or opaque.

The virtual object may be a three dimensional virtual object. The virtual object may be in free space, and/or may be physically unsupported.

The interaction zone may be defined geometrically. The interaction zone may be defined around at least a portion of the virtual object, may be defined to enclose a majority of the virtual object, and/or may enclose substantially all of the virtual object. The interaction zone may be larger than the virtual object.

The interaction zone may be defined as a three dimensional enclosing surface. The interaction zone may be defined as a three dimensional volume. The interaction zone may be defined as a radius from a point substantially central to the virtual object. The interaction zone may be defined as a distance from a surface of the virtual object. The interaction zone may be defined to be larger than the virtual object by at least the uncertainty in the position of the virtual object. The interaction zone may be defined to be larger than the virtual object by at least the uncertainty in the relative distance between the virtual object and an end-effector.

The interaction zone may maintain a radial dimension at least equal to the sine of an angle having a vertex at an end-effector. The angle may be approximately 5 degrees, may be approximately 2.5 degrees, or may be approximately 1 degree.

The interaction zone may be definable by the user. The interaction zone may be invisible.

The user may deliver the stimulus to the interface. The stimulus may be defined to include contacting the interaction zone with an end-effector. The stimulus may be defined to include approaching the virtual object with an end-effector while the effector is within the interaction zone. The stimulus may defined to include disposing an end-effector within the interaction zone for a time period. The stimulus may be defined to include moving an end effector proximate the virtual object while the end-effector is within the interaction zone. The stimulus may be defined to include pointing an end-effector at the virtual object while the end-effector is within the interaction zone.

The method may include defining the stimulus as a discrete event and/or as an ongoing condition. The method may include defining the response as a discrete event and/or as an ongoing condition.

The response may be defined to include engaging the virtual object with an end-effector. The response may be defined to include executing a function associated with the object. The response may be defined to include running a program associated with the virtual object. The response may be defined to include moving the virtual object towards an end-effector. The response may be defined to include aligning the virtual object with an end-effector. The response may be defined to include linking the virtual object with an end-effector, such that the virtual object moves with the end-effector. The response may be defined to include changing the status of the virtual object from sleep mode to active mode. The response may be defined to include redefining the interaction zone.

The response may include transmitting feedback to the user. The feedback may include a change in color, saturation, contrast, transparency, size, and/or luminosity. The feedback may include sound, vibration, heat, cold, and/or light.

One or more of the steps of defining the interaction zone, defining the stimulus, defining the response, sensing the stimulus, and/or executing the response may be controlled by an operating system, by a program associated with the virtual object, by the virtual object, and/or by the user.

The method may include determining the position of an end-effector relative to the virtual object, and defining the interaction zone such that the extent of the interaction zone beyond the virtual object is at least as large as the uncertainty in the position of the end-effector relative to the virtual object. When the end-effector applies a stimulus to the interaction zone, the response is executed as though the end-effector had applied the stimulus to the virtual object.

Two or more responses may be executed. Responses may be executed in sequence and/or in parallel. The method may include sensing two or more stimuli, and executing responses to each of those stimuli.

The method may include defining a first interaction zone and a second interaction zone, the second interaction zone being defined closer to the virtual object than the first interaction zone, and generating the first and second interaction zones. The method may include defining a first stimulus of the first interaction zone and a second stimulus of the second interaction zone. When the first stimulus is sensed the first response is executed, and when the second stimulus is sensed the second response is executed.

The method may include defining the first and second stimuli as ongoing conditions. The first response is executed if the first stimulus is sensed, and continues to be executed until the first stimulus is no longer sensed. The second response is executed if the second stimulus is sensed, and continues to be executed until the first stimulus is no longer sensed.

The first response may be a sensory enhancement of the virtual object, and the second response may be engagement of the virtual object.

The first and/or second stimulus may be a discrete event.

In another embodiment of the present invention, an apparatus is provided for interacting with a three dimensional interface. The apparatus includes a processor adapted to generate a three dimensional interface, to generate at least one virtual object in the interface, and to define an interaction zone associated with the virtual object. The apparatus also includes a display in communication with the processor, the display being adapted to output the three dimensional interface and virtual object. At least one sensor is in communication with the processor, the sensor being adapted to detect a stimulus of the interaction zone. The processor is adapted to generate a response signal when a stimulus is communicated to the processor by the sensor.

The display may be a stereo display.

The sensor may be adapted to sense the three dimensional position of an end effector relative to the interaction zone, and/or to sense the three dimensional motion of an end effector relative to the interaction zone. The sensor may be a stereo sensor, and/or may be an image sensor.

The response signal may instruct a change in the color, saturation, contrast, transparency, size, and/or luminosity of the virtual object. The processor may be adapted to execute the change. The response signal may instruct generation sound, vibration, heat, cold, and/or light.

The apparatus may include a response executor in communication with the processor, the executor being adapted to execute a response based on the response signal. The executor may be adapted to generate sound, vibration, heat, cold, and/or light. The executor may be physically unconnected to the processor. The executor may be disposed on an end-effector. The executor may be a stylus.

The processor, display, and sensor may be disposed on a wearable device. The processor, display, and sensor may be disposed on a head mounted display.

In another embodiment of the present invention, a method is provided for interacting with a three dimensional interface. The method includes generating, in a processor, a stereo three dimensional interface, generating at least one three dimensional virtual object disposed in free space in the interface, and defining a three dimensional geometric interaction zone enclosing substantially all of the virtual object. The method further includes sensing a stimulus of the interaction zone, the stimulus including contact between the interaction zone and an end-effector. The method includes executing a response to the stimulus, the response including a change in the color, saturation, contrast, transparency, size, and/or luminosity of the virtual object.

In another embodiment of the present invention, an apparatus is provided for interacting with a three dimensional interface. The apparatus includes a processor adapted to generate a stereo three dimensional interface, to generate at least one virtual object in the interface, and to define a three dimensional interaction zone enclosing substantially all of the virtual object. The apparatus includes a display in communication with the processor, the display being adapted to output the stereo three dimensional interface and the virtual object. At least one image sensor is in communication with the processor, the sensor being adapted to detect a stimulus of the interaction zone, the stimulus including contact between the interaction zone and an end-effector. The processor is adapted to generate a response signal when the stimulus is communicated to the processor by the sensor, the response including a change in the color, saturation, contrast, transparency, size, and/or luminosity of the virtual object.

In another embodiment of the present invention, an apparatus is provided for interacting with a three dimensional interface. The apparatus includes means for generating a three dimensional interface, means for generating at least one virtual object in the interface, means for defining an interaction zone associated with the virtual object, and means for generating the interaction zone. The apparatus also includes means for defining a stimulus of the interaction zone, means for defining a response to the stimulus, means for sensing the stimulus of the interaction zone, and means for executing the response if the stimulus is sensed.

BRIEF DESCRIPTION OF THE SEVERAL VIEWS OF THE DRAWINGS

Like reference numbers generally indicate corresponding elements in the figures.

DETAILED DESCRIPTION OF THE INVENTION

Figure 1:
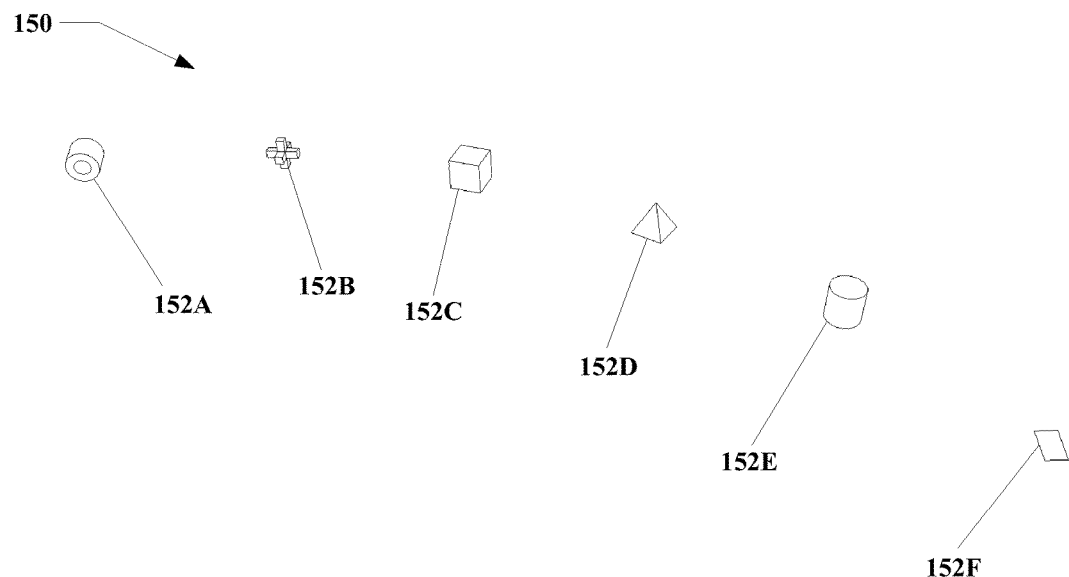
FIG. 1 shows an embodiment of a three dimensional interface in accordance with the present invention.

Referring to FIG. 1, an embodiment of a three dimensional interface 150 in accordance with the present invention is shown. The interface 150 includes at least one virtual object 152.

As illustrated, the interface in FIG. 1 includes six virtual objects, 152A through 152F, but in practice the number of virtual objects 152 may be more or less than shown. The number of virtual objects 152 may also vary over time for a given interface 150. For example, virtual objects may be added, moved, deleted, etc. by the user, the operating system, and/or other agencies.

The present invention also is not particularly constrained with respect to the type of virtual objects 152 that may be incorporated into the interface 150. For simplicity, virtual objects 152A through 152F are shown as geometric shapes. However, graphical icons, still images, animations, constructs of fixed and moving sub-components, and other entities may also be suitable. In addition, the term "virtual object" as used herein may encompass entities that might not be considered to be objects in a strict sense if such "objects" were physical, e.g. light sources, puffs of virtual smoke, cascading streams of virtual water, etc. Virtual objects may be opaque, translucent, or transparent, or some combination thereof. Virtual objects may include auditory and/or other sensory information as well. The term "virtual object" as used herein should be taken to represent any virtual construct that can be represented to a user within the interface.

In particular, it is noted that virtual objects 152 within the three dimensional interface 150 may be three dimensional virtual objects. However, this is not required; while virtual objects 152A through 152E in FIG. 1 are shown as three dimensional objects, virtual object 152F is a two dimensional object. Virtual objects 152 are not particularly limited with regard to the number of dimensions they exhibit.

For some embodiments, the three dimensional interface 150 may be a transparent interface. That is, regions not occupied by the virtual objects 152 or other features of the interface 150 may be partially or fully transparent, such that the physical world surrounding the interface 150 is partially or fully visible therethrough to a user. Alternately, the unoccupied regions of the three dimensional interface 150 may be partially or fully opaque, such that some or all of the user's view of the user's physical surroundings is obscured.

Figure 2:
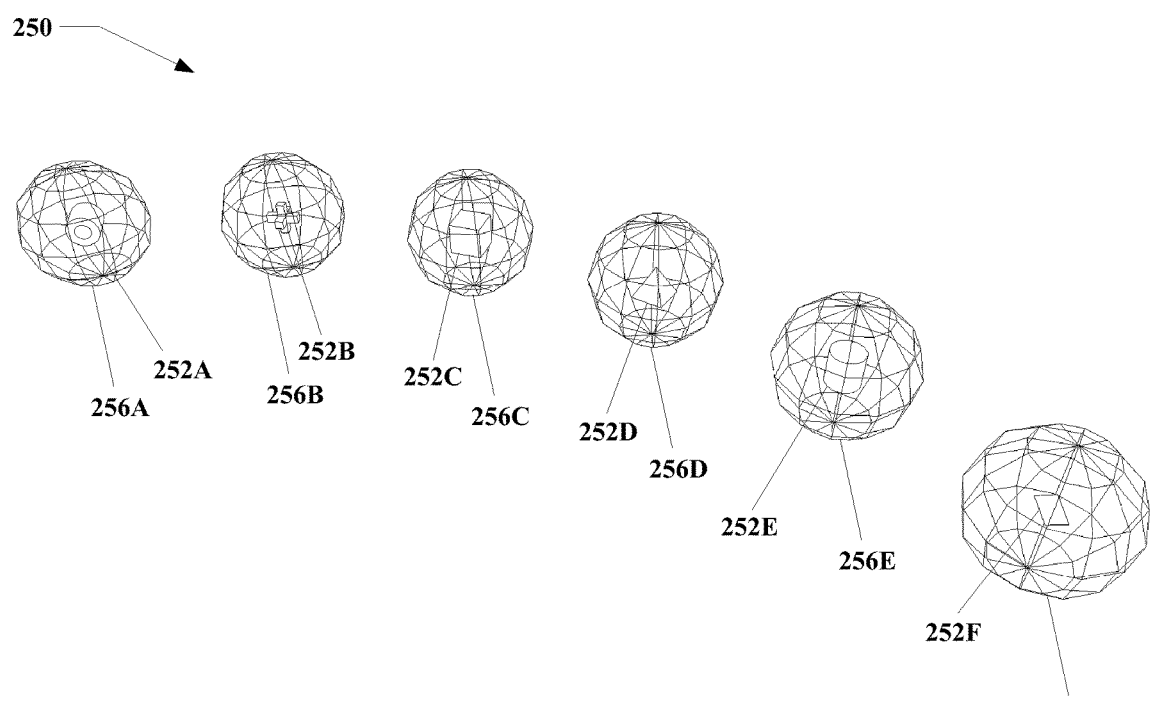
FIG. 2 shows an embodiment of a three dimensional interface in accordance with the present invention, with interaction zones around objects therein.

FIG. 2 shows an interface 150 visually similar to that of FIG. 1, however in FIG. 2 the interface is illustrated with interaction zones 256A through 256F, defined around virtual objects 252A through 252F. Typically, though not necessarily, the interaction zones 256 in a particular interface 250 are invisible to the user. However, interaction zones 256 are depicted visually (e.g. as wireframes) in FIG. 2 and elsewhere herein for clarity.

In addition, it is noted that virtual objects 252A through 252F and interaction zones 256A through 256F may be, and typically are, entirely non-physical. That is, virtual objects 252 and interaction zones 256 are not required to have physical substance in and of themselves. Virtual objects 252 and/or interaction zones 256 may be outputted so as to appear in free space, that is, so as not to overlap with or contact physical objects and/or structures in the physical world (though such contact and/or overlapping is not excluded). Likewise, virtual objects 252 and/or interaction zones 256 are not required to be physically supported by objects, surfaces, and/or forces in the physical world, nor do virtual objects 252 and interaction zones 256 necessarily correspond to physical objects and/or surfaces in the physical world. Although the three dimensional interface 250 may or may not be outputted in such a way as to appear to occupy a volume that also contains physical objects, structures, etc., the virtual objects virtual objects 252 and/or interaction zones 256 are not required to be associated with physical objects.

Turning to FIG. 3A through FIG. 3D, therein is shown a stimulus to an interaction zone 356C and a response to that stimulus. For simplicity, a single virtual object 352C is shown, visually similar to a portion of FIG. 2, along with an interaction zone 356C defined around the virtual object 352C. In addition, for illustrative purposes, one portion of the interaction zone 356C is illustrated as being both opaque and hatched. Although as noted above the interaction zone 356C may be invisible, it is shown here to help indicate interactions between the interaction zone 356C and an end-effector 354.

With regard to the end-effector 354, as used herein the term end-effector refers to an entity used for manipulation, often though not exclusively based on the position, orientation, and/or configuration of an end of that entity. As illustrated in FIG. 3A through FIG. 3D, the end-effector 354 is a stylus. A stylus is a convenient end-effector 354 for certain embodiments of the present invention. A stylus 354 is also convenient for illustrative purposes, in that a stylus 354 can be made to have a simple configuration and a well-defined point that can be used to clearly identify interactions with other entities, such as a virtual object 352C, in illustrations. However, other end-effectors, including but not limited to fingers, hands, mice, etc. or even ad hoc end-effectors such as pens, pencils, water bottles, etc. may be used to interact with the interface 350 in some embodiments. In addition, it is noted that end-effectors are not limited only to solid objects, or to real-world entities. For example, for some embodiments a light beam may be a suitable end-effector. For other embodiments, a virtual construct, object, or effect may be a suitable end-effector.

It is noted that the end-effector 354 as shown in FIG. 3A through FIG. 3D is used to manipulate the interface, but the end-effector 354 may not necessarily be considered part of the interface 350 itself.

For purposes of description with regard to FIG. 3A through FIG. 3D, stimulus of the interaction zone 356C should be understood to be contact between the end-effector 354 and the interaction zone 356C. However, as is also described elsewhere, this is an example only, and other stimuli may be equally suitable.

Figure 3A:
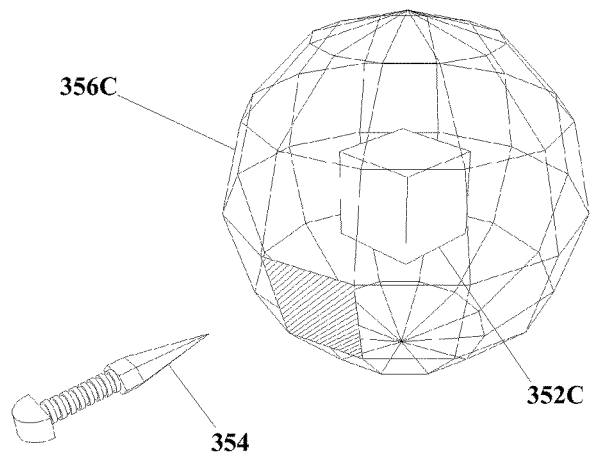
FIG. 3A through FIG. 3D show an end-effector interacting with a virtual object in accordance with the present invention.

With reference specifically to FIG. 3A, the virtual object 352C, the interaction zone 356C around the virtual object 352C, and the end-effector 354 are shown, with the end-effector 354 some distance away from the interaction zone 356C. In this arrangement, the end-effector 354 is not touching, and thus is not stimulating, the interaction zone 356C.

Figure 3B:
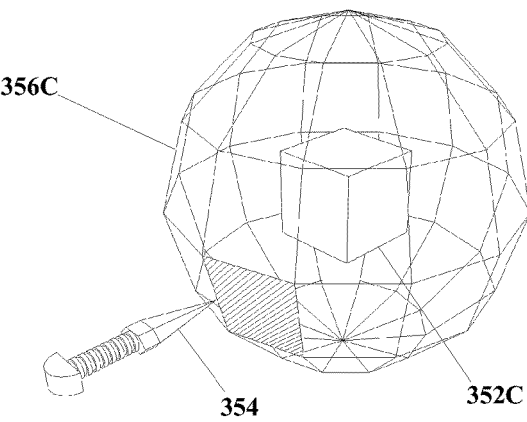

In FIG. 3B, the end-effector 354 is approaching the interaction zone 356C. However, the end-effector 354 still has not reached the interaction zone 356C, and so the end-effector 354 still is not stimulating the interaction zone 356C.

Figure 3C:
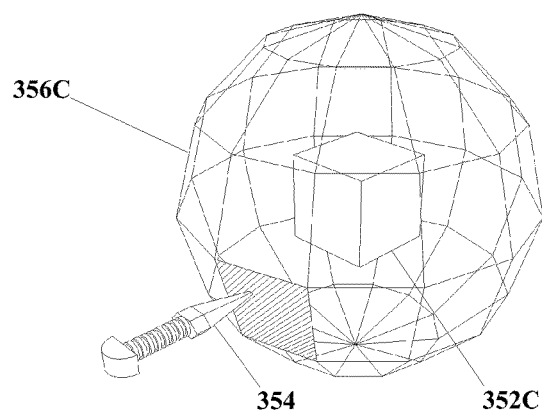

FIG. 3C shows an arrangement wherein the end-effector 354 has reached the interaction zone 356C. As may be seen, the tip of the end-effector 354 has entered the hatched portion of the interaction zone 356C. For the embodiment under consideration, this contact between the end-effector 354 and the interaction zone 356C constitutes a stimulus of the interaction zone 356C.

Figure 3D:
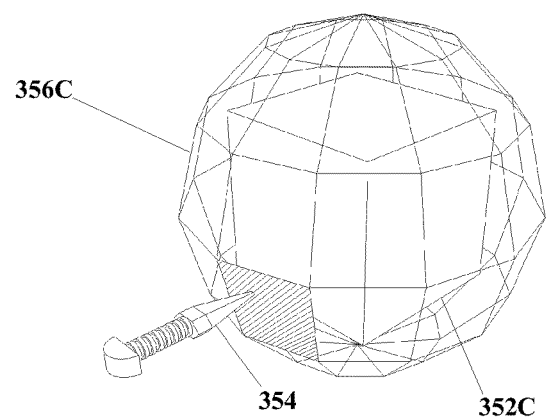

FIG. 3D shows an example of a response to the stimulus that is shown being delivered in FIG. 3C. As illustrated, the virtual object 352C has increased in size, in response to the stimulus to the interaction zone 356C.

In defining an interaction zone 356C around a virtual object 352C, sensing a stimulus of the interaction zone 356C, and executing a response to the stimulus, a number of advantages are achieved, including but not limited to the following.

It is possible through the present invention to interact with a three dimensional interface, and with virtual objects therein, without necessarily making direct contact with those virtual objects (or with other features of the virtual interface). By defining an interaction zone around a virtual object, and by sensing and responding to stimuli of that interaction zone, it is possible to produce an effect of having directly contacted that virtual object without difficulties associated with directly contacting a virtual object in a three dimensional interface.

By enabling a user to address a virtual object by addressing its interaction zone, it becomes possible to define the interaction zone to improve the usability and/or functionality of the three dimensional interface. For example, for certain embodiments it may be useful to define the interaction zones for some or all virtual objects so as to be significantly larger than the virtual objects themselves. In such a case, a user would not be required to, for example, align an end effector precisely with a virtual object; rather, the user could interact with that virtual object by aligning the end-effector with the interaction zone, which being larger may require less precision on the part of the user.

Similarly, given such an arrangement with interaction zones significantly larger than their associated virtual objects, the need for precision by the controlling system may be lessened.

For example, while a conventional system generating a three dimensional virtual interface may have data indicating with precision where any virtual objects in that interface are located, errors in the apparent positions of those objects may occur as the interface is outputted to the user. Likewise, conventionally errors may occur in determining the position of an end-effector (if present) used to interact with the three dimensional interface based on sensor input. From these and other sources, there may be uncertainty in determining whether, for example, an end-effector contacts a specific virtual object.

However, with the present invention, a user may interact with a virtual object by interacting with an interaction zone defined for that object. While similar positional uncertainty may exist in the present invention, the interaction zone can be defined to make such uncertainty less significant and/or less noticeable. For example, given the arrangement described above with interaction zones defined to be significantly larger than their associated virtual objects, that larger size for the interaction zones may compensate for uncertainty in the relative positions of an end-effector and a virtual object. In essence, the interaction zone, when so defined, may serve as a buffer for uncertainties in position, in addition to its other functions. Thus, highly precise determinations of where virtual objects are, where an end-effector is, etc. become less significant to the smooth operation of the three dimensional interface.

In particular, it may be possible for some embodiments to measure, estimate, or otherwise determine a typical level of uncertainty in position, and define an interaction zone so as to be at least as large as that uncertainty. For example, the interaction zone for a virtual object could be defined so as to be larger than the virtual object itself by at least the uncertainty in the position of that virtual object. Alternately, for embodiments utilizing an end-effector, the interaction zone for a virtual object could be defined so as to be larger than the uncertainty in the relative distance between/positions of the end-effector and the virtual object.

In addition, defining an interaction zone enables additional functionality. Where direct contact with a virtual object is essentially a binary process—either there is contact, or there is no contact—an interaction zone may be defined so as to enable multiple responses, behaviors, and/or other features when, for example, an end-effector approaches a particular virtual object, as the end-effector contacts the virtual object, as the end-effector recedes from the virtual object, as the end-effector moves relative to the virtual object, etc. This may provide a richer, more flexible interaction with a three dimensional interface than would a simple binary "contact/no contact" arrangement.

For example, for embodiments wherein an interaction zone extends beyond an associated virtual object in at least one direction, the present invention enables interaction with the virtual object without necessarily contacting the virtual object at all.

Returning to the examples of FIG. 3A through FIG. 3D, the interaction zone 356C is defined therein as a roughly spherical geometric surface, the stimulus to the interaction zone 356C is a contact stimulus an end-effector 354, and the response to the stimulus is a change in size of the virtual object 352C. However, these are examples only.

A number of approaches for defining the interaction zone 356C may be suitable. For example, the interaction zone 356C may be defined as an enclosing three dimensional surface, wherein to stimulate that three dimensional surface is to stimulate the interaction zone 356C. This is the arrangement illustrated in FIG. 3A through FIG. 3D.

However, for other embodiments it may be suitable to define the interaction zone 356C as a volume, rather than as a surface. This is potentially useful if, for instance, the interaction zone 356C is large compared to the end-effector 354, or to the portion of the end-effector that is considered for purposes of determining whether a stimulus is present. For a sufficiently large interaction zone 356C and/or a sufficiently small end-effector 354 it may be possible to dispose an end-effector 354 entirely inside of the interaction zone 356C, such that an interaction zone 356C defined as a shell might no longer be considered to be in contact with the end effector 354, and thus the interaction zone 356C might no longer be considered to be stimulated. This may be avoided through the definition of an interaction zone 356C as a volume.

Alternately, an interaction zone 356C might be defined by distance rather than by a particular geometric form. For example, the interaction zone 356C may be defined as a maximum distance from one or more points in or on the virtual object 352C. One such approach would be to define a point that is substantially central to the virtual object 352C, and define a radius from that point such that if an end effector 354 approaches the defined point to within the defined radius, this would constitute stimulus of the interaction zone 356C. Although such an arrangement would produce a substantially spherical interaction zone 356C, other similar arrangements could be implemented that would produce interaction zones 356C of any arbitrary shape, e.g. cylinders, ovoids, toroids, etc.

Another variation on such a distance-based approach would be to define an interaction zone 356C in terms of a distance from the surface of a virtual object 352C. This would result in an interaction zone 356C having a shape that substantially conforms to the shape of the virtual object 352C itself.

Although the interaction zone 356C may be substantially aligned center-to-center with its associated virtual object 352C, this is not required. Arrangements wherein an interaction zone 356C is offset from the virtual object 352C may be equally suitable.

Typically, the interaction zone 356C for a given virtual object 352C will be larger than the virtual object 352C, and/or will enclose all or substantially all of that virtual object 352C. However, this is not required. Arrangements wherein the interaction zone 356C encloses a majority of the virtual object 352C, or only a part of the virtual object 352C, or even wherein the interaction zone 356C does not enclose any part of the virtual object, 352C, may be equally suitable. In particular, for certain applications it may be useful to define gaps or apertures within an interaction zone 356C, whether the interaction zone 356C is defined as a shell, as a volume, as a distance, etc. Likewise, for certain embodiments the interaction zone 356C may be smaller in total volume, diameter, or some other measurement standard than the associated virtual object 352C.

Figure 4:
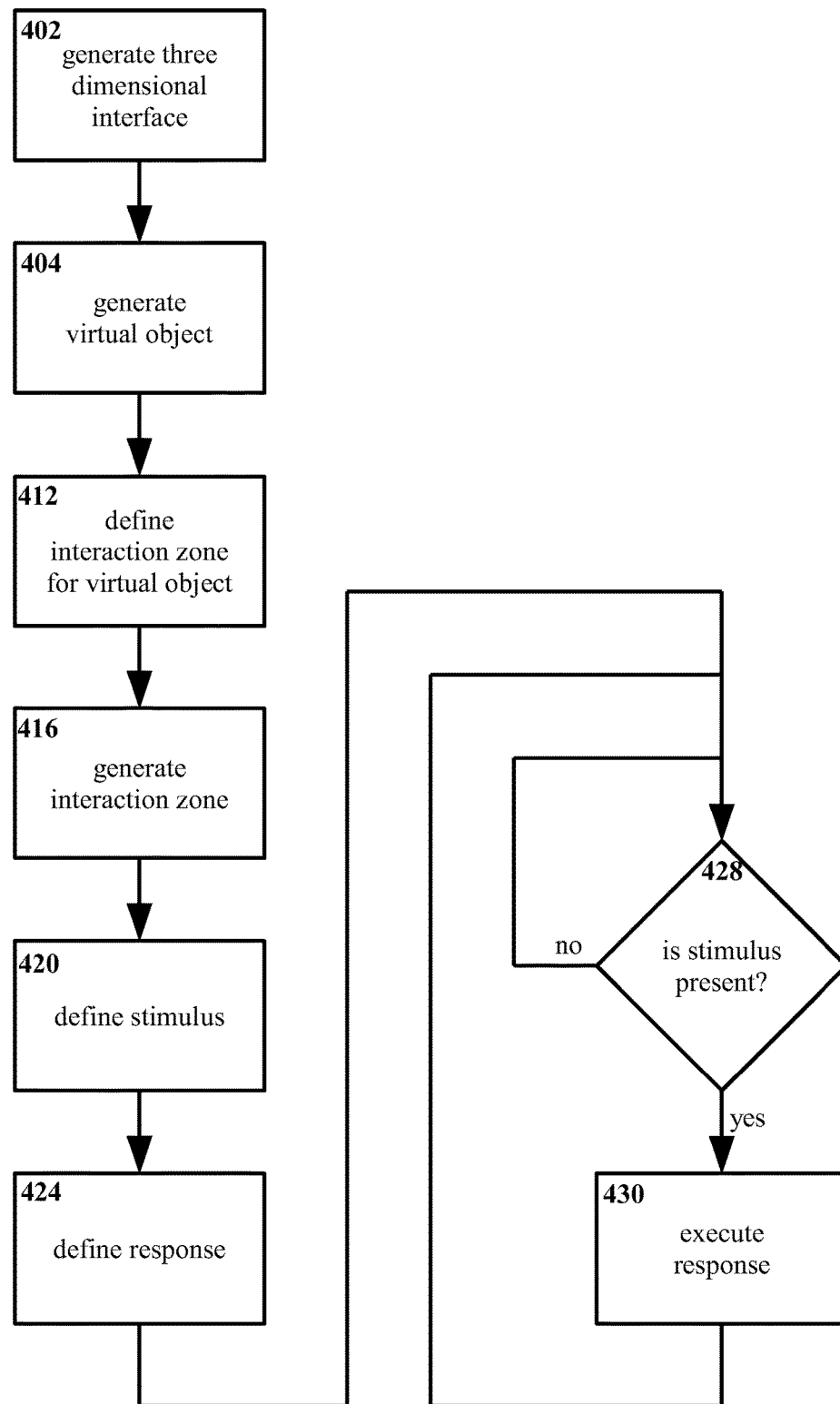
FIG. 4 shows an embodiment of a method for managing interaction with a three dimensional interface in accordance with the present invention.

Turning to FIG. 4, a flowchart of an embodiment of a method for handling interaction with a three dimensional interface in accordance with the present invention is shown therein. The steps shown in FIG. 4 may be implemented through the use of executable instructions on a processing system, however, the present invention is not particularly limited insofar as the mechanisms for executing these method steps.

In the method of FIG. 4, a three dimensional interface is generated 402 in a processor. At least one virtual object is generated 404 in the three dimensional interface. For purposes of clarity, only one virtual object is considered in this example, but the method is applicable to an arbitrary number of such virtual objects.

An interaction zone is defined 412 for the virtual object. That interaction zone is then generated 416. As noted elsewhere herein, the interaction zone may be defined 412 in many ways, and the present invention is not particularly limited with regard to how the interaction zone is defined 412.

It is noted that generating the interaction zone 416 does not necessarily imply that the interaction zone is made visible within the interface. The interaction zone may be invisible, intangible, etc. In generating the interaction zone 416, the interaction zone is incorporated into the three dimensional interface as an operating feature thereof.

Moving onward, a stimulus is defined 420 for the interaction zone. Also, a response is defined 424 for the interaction zone, such that when the stimulus is present the response is executed. As also described elsewhere herein, both the stimulus and the response may be defined 420 and 424 in many ways, and the present invention is not particularly limited in terms of how the stimulus and the response are defined 420 and 424.

A determination is made 428 as to whether or not the stimulus is present. That is, is the stimulus as defined 420 being applied to the interaction zone as defined 412 and generated 416? If the stimulus is not determined 428 to be present, the method repeats the determination 428.

If the stimulus is determined 428 to be present, the response is executed 430. The response having been executed 430, the method repeats the determination 428.

It will be understood that the loop of detecting the stimulus 428 and executing the response 430 may be implemented in various ways. For example, when the stimulus is detected 428, the response may be executed 430 a single time; the response may be executed 430 repeatedly while the stimulus is detected 428; the response may be executed 430 and sustained for so long as the stimulus is detected; etc. These and/or other arrangements may be possible depending in part on precisely how the interaction zone is defined 412, how the stimulus is defined 420, and/or how the response is defined 424.

Figure 5:
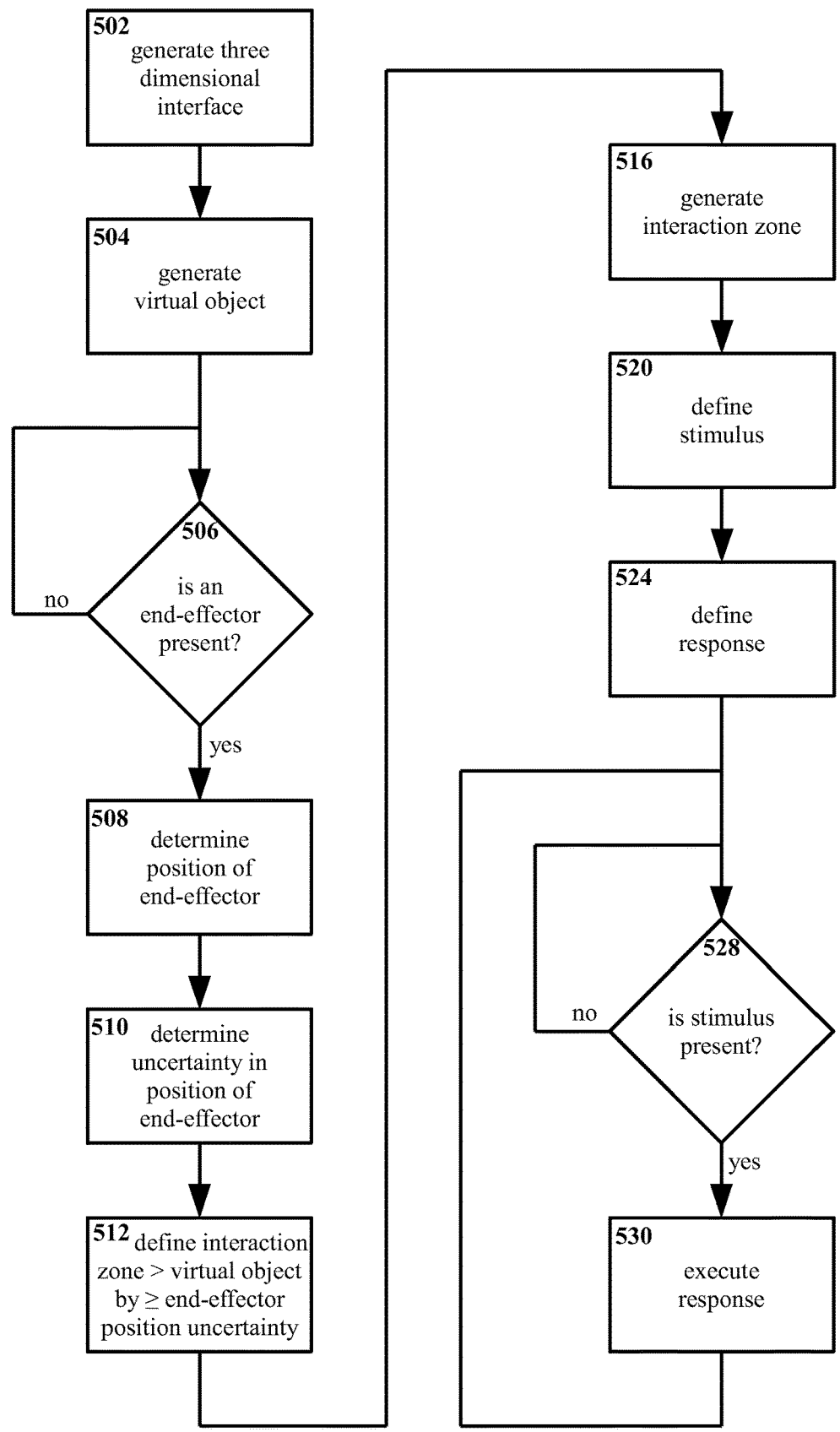
FIG. 5 shows an embodiment of a method for managing interaction with a three dimensional interface in accordance with the present invention, incorporating determination of position uncertainty of an end-effector.

Turning to FIG. 5, it will be seen that the interaction zone may be defined at least in part by local conditions and/or parameters. FIG. 5 shows a flowchart of another embodiment of a method for handling interaction with a three dimensional interface in accordance with the present invention.

In the method shown in FIG. 5, a three dimensional interface is generated 502 in a processor. At least one virtual object is generated 504 in the three dimensional interface.

A determination is made 506 as to whether an end-effector is present (e.g. within the region occupied by the interface, near to the interface region, etc.). If no end-effector is present, the method repeats the determination 506.

If an end effector is determined 506 to be present, the position of the end-effector is determined 508. A degree of uncertainty in the position of the end-effector is also determined 510. The present invention is not particularly limited with regard to how the position and/or degree of uncertainty in the position of the end-effector are determined 508 and 510. For example, the degree of uncertainty may be the uncertainty in the absolute position of the end-effector, or might be the uncertainty in the relative position of the end-effector with respect to the virtual object, or with respect to some sensing device such as a camera, with respect to a defined "origin" position for the three dimensional interface, etc.

With the degree of uncertainty in the position of the end-effector determined 510, the interaction zone 512 is defined. More particularly, the interaction zone is defined 512 such that the interaction zone is larger than the virtual object, by at least as much as or more than the uncertainty in the position of the end-effector. Thus, if the uncertainty were a linear distance of 3 mm, the interaction zone would be defined 512 to extend at least 3 mm beyond the virtual object; if the uncertainty were an angular distance of 0.5 degrees, the interaction zone would be defined 512 to extend at least 0.5 degrees beyond the virtual object; etc.

Thus, local conditions and/or parameters, in this example the uncertainty in the position of the end-effector, can be incorporated into the method. For this example, it will be understood that in defining the interaction zone 512 to be larger than the virtual object by at least the uncertainty determined 510 for the position of the end-effector, the interaction zone can be used to compensate for positional uncertainty. The interaction zone could, in this example, serve as a "buffer", so that the virtual object could respond to user interactions via the end-effector (i.e. a stimulus to the interaction zone could be sensed and a response executed) even if the position of the end-effector and/or the virtual object are not known with perfect precision.

Moving on, with the interaction zone so defined 512, the interaction zone is generated 516. A stimulus is defined 520 for the interaction zone, and a response is defined 524 for the interaction zone, such that when the stimulus is present the response is executed. A determination is made 528 as to whether or not the stimulus is present. If the stimulus is not determined 528 to be present, the method repeats the determination 528.

Figure 6A:
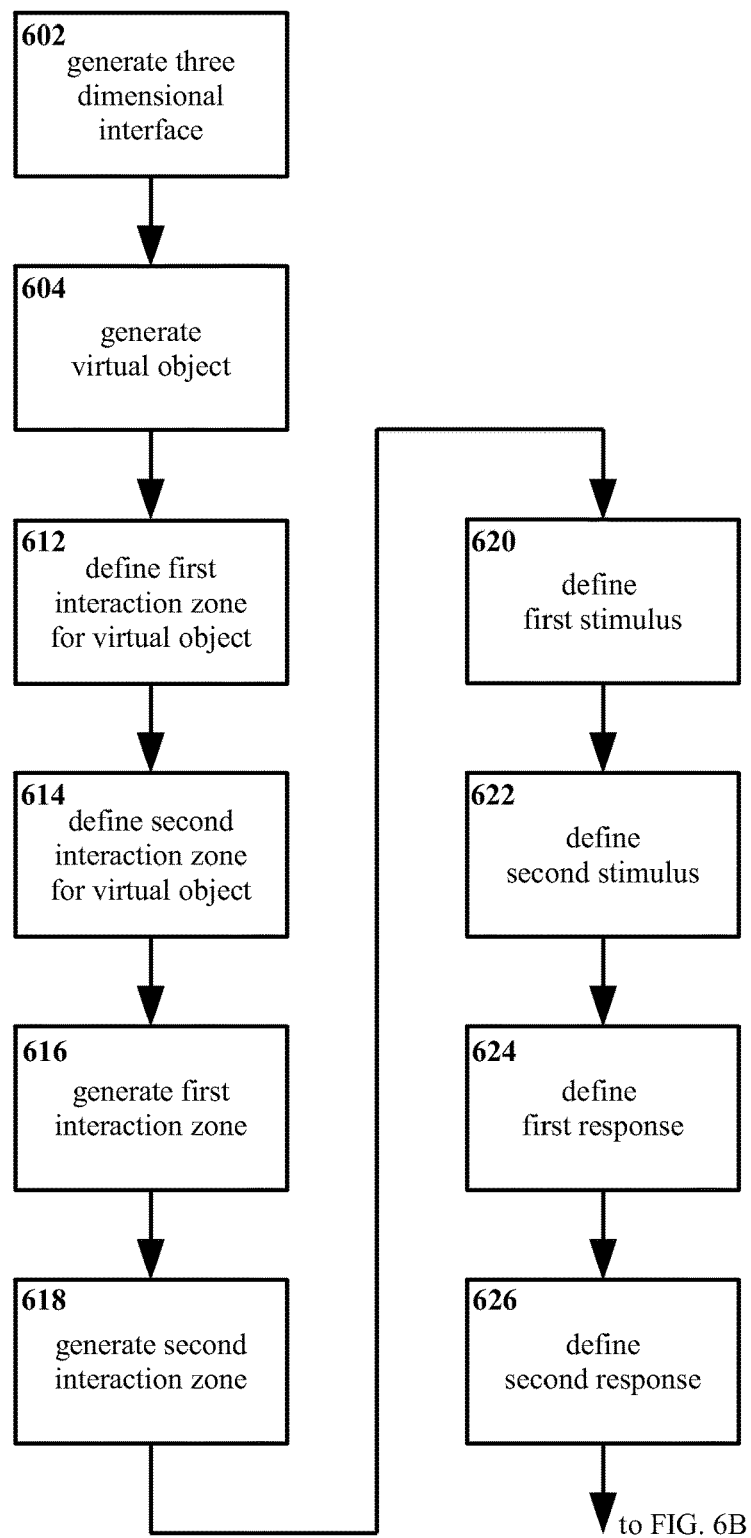
FIG. 6A and FIG. 6B show an embodiment of a method for managing interaction with a three dimensional interface in accordance with the present invention, utilizing first and second interaction zones.
Figure 6B:
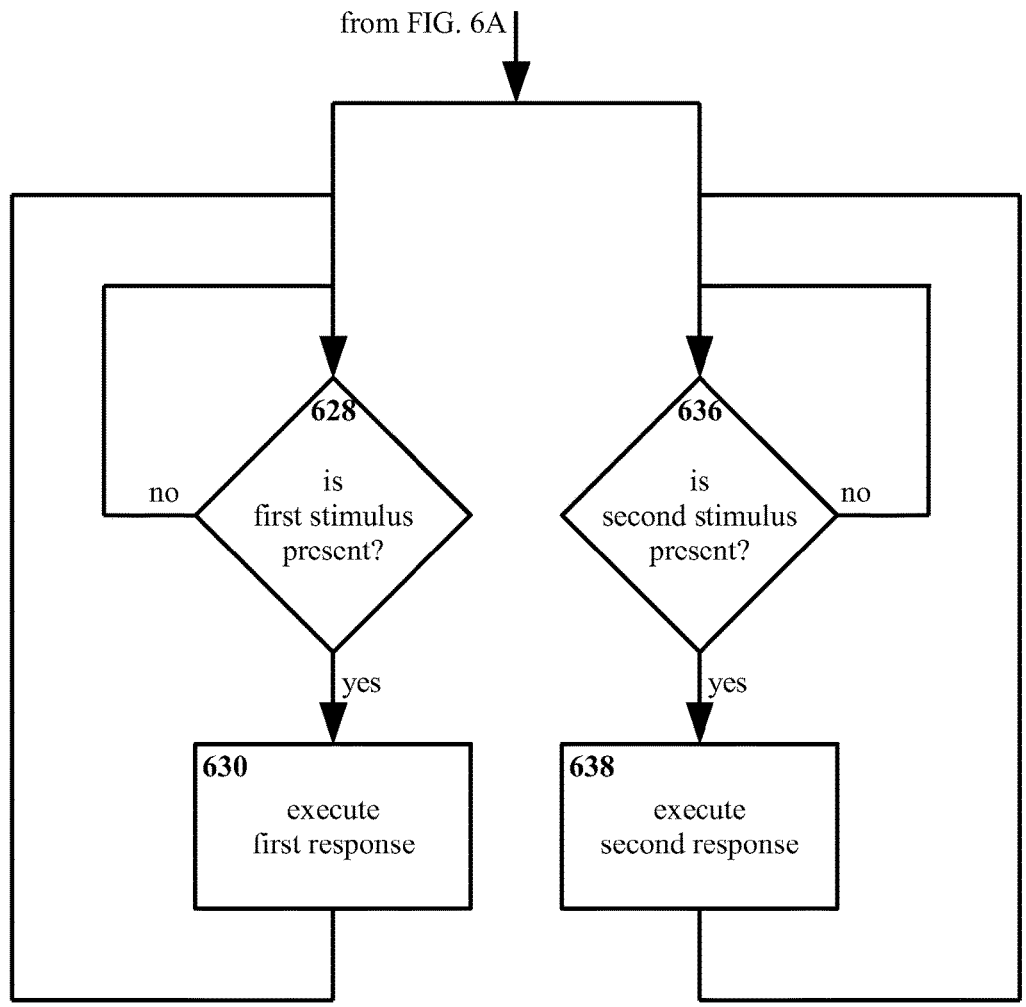

Turning to FIG. 6A and FIG. 6B, a flowchart is shown of another embodiment of a method for handling interaction with a three dimensional interface in accordance with the present invention.

The present invention is not limited to one interaction zone per virtual object, or to one stimulus/response arrangement. FIG. 6A and FIG. 6B show a method that utilizes first and second interaction zones.

Beginning with FIG. 6A, a three dimensional interface is generated 602. At least one virtual object is generated 604 in the three dimensional interface.

A first interaction zone is defined 612 for the virtual object. A second interaction zone is also defined 614 for the virtual object. The first and second interaction zones are generated 616 and 618.

A first stimulus is defined 620 for the first interaction zone, and a second stimulus is defined 622 for the second interaction zone. Also, a first response is defined 624 for the first interaction zone, such that when the first stimulus is present the first response is executed; and a second response is defined 626 for the second interaction zone, such that when the second stimulus is present the second response is executed.

Continuing with FIG. 6B, the method follows two loops in parallel.

In a first loop, a determination is made 628 as to whether or not the first stimulus is present. If the first stimulus is not determined 628 to be present, the method repeats the determination 628 in the first loop. However, if the first stimulus is determined 628 to be present, the first response is executed 630. The first response having been executed 630, the method repeats the determination 628 in the first loop.

Similarly, in a second parallel loop, a determination is made 636 as to whether or not the second stimulus is present. If the second stimulus is not determined 636 to be present, the method repeats the determination 636 in the second loop. However, if the second stimulus is determined 636 to be present, the second response is executed 638. The first response having been executed 638, the method repeats the determination 636 in the first loop.

In the arrangement shown in FIG. 6A and FIG. 6B, the first and second interaction zones function independently of one another. That is, the first interaction zone may receive the first stimulus, and the first response executed, regardless of whether or not the second interaction zone has received the second stimulus and/or the second response has been executed.

However, such an arrangement is an example only. Where multiple interaction zones, multiple stimuli, and/or multiple responses are utilized, the interaction zones, stimuli, and/or responses may be independent as shown in FIG. 6A and FIG. 6B, but in other embodiments it may be equally suitable for interaction zones, stimuli, and/or responses to be related.

Figure 7A:
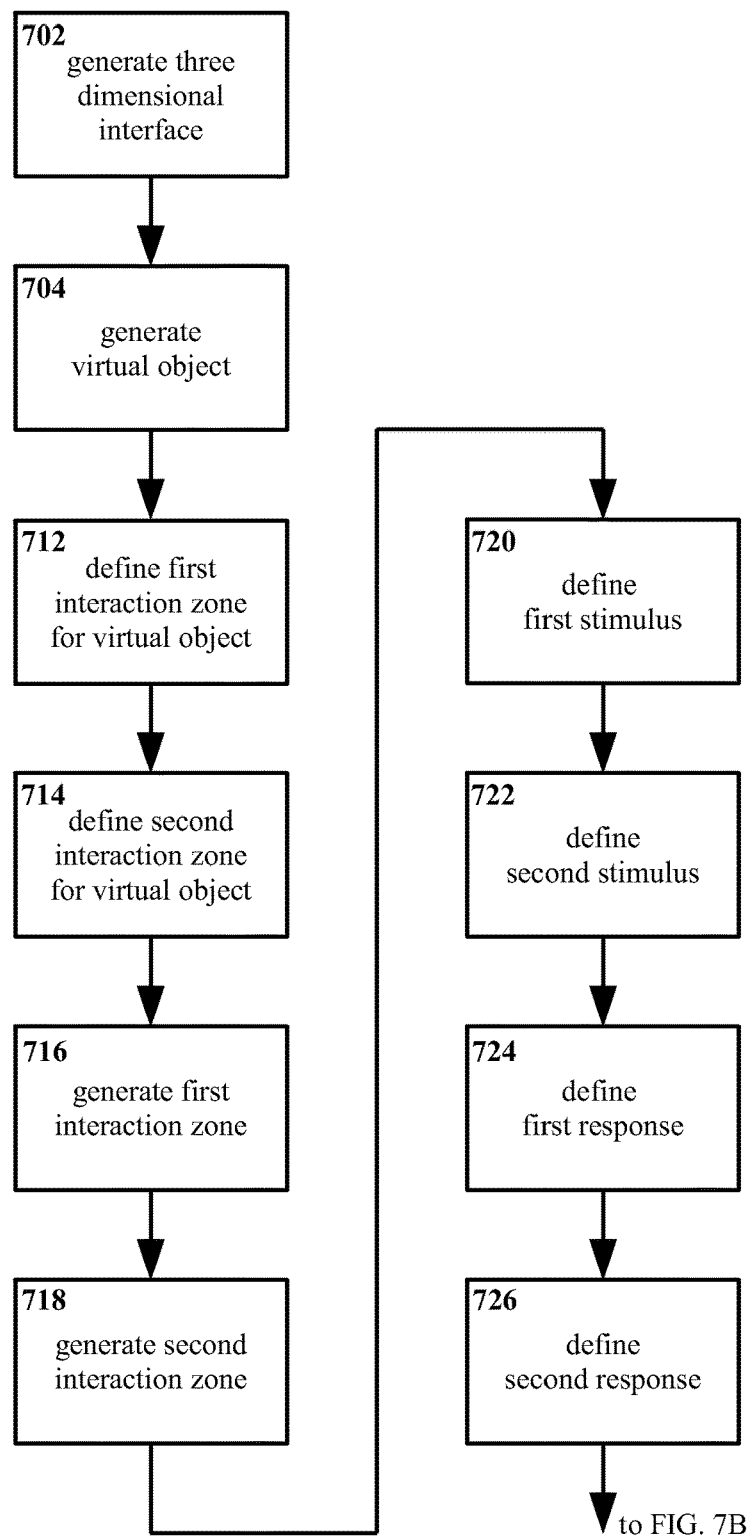
FIG. 7A and FIG. 7B show another embodiment of a method for managing interaction with a three dimensional interface in accordance with the present invention, also utilizing first and second interaction zones.
Figure 7B:
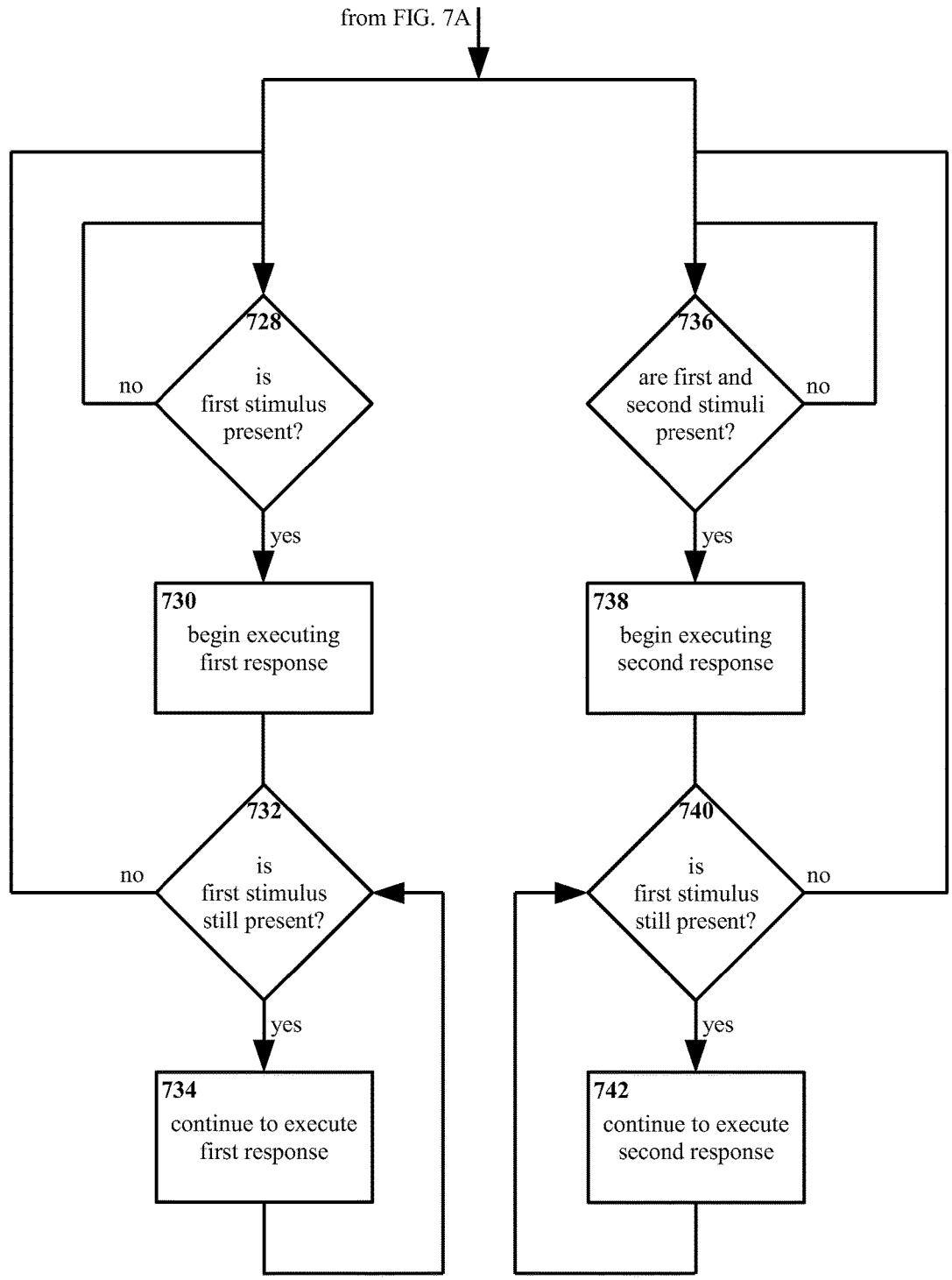

For example, FIG. 7A and FIG. 7B show a method that utilizes first and second interaction zones, wherein the second interaction zone functions in a fashion that is at least in part dependent upon the first interaction zone.

Beginning with FIG. 7A, a three dimensional interface is generated 702. At least one virtual object is generated 704 in the three dimensional interface.

A first interaction zone is defined 712 for the virtual object. A second interaction zone is also defined 714 for the virtual object. The first and second interaction zones are generated 716 and 718.

A first stimulus is defined 720 for the first interaction zone, and a second stimulus is defined 722 for the second interaction zone. Also, a first response is defined 724 for the first interaction zone, such that when the first stimulus is present the first response is executed; and a second response is defined 726 for the second interaction zone, such that when the second stimulus is present the second response is executed.

Continuing with FIG. 7B, the method follows two loops in parallel.

In a first (leftmost) loop, a determination is made 728 as to whether or not the first stimulus is present. If the first stimulus is not determined 728 to be present, the method repeats the determination 728 in the first loop. However, if the first stimulus is determined 628 to be present, the first response is executed 730.

Continuing the first loop, once the first response is executed 730 a determination is made 732 as to whether the first stimulus is still present. If the first stimulus is not determined 732 to be still present, the method returns back to step 728. However, if the first stimulus is determined 732 to be still present, the first response continues to be executed 734.

It is noted that the first loop, steps 728 through 734, may be considered to be a more detailed and explicit example of a stimulus-response arrangement already described with regard to FIG. 4. Namely, as noted with regard to FIG. 4, when a stimulus is detected the response may be executed repeatedly while the stimulus is detected. However, as noted already with respect to FIG. 4, such an arrangement is an example only; it is presented in FIG. 7 for illustrative purposes.

Returning to FIG. 7B and moving on to the second (rightmost) loop, a determination is made 736 as to whether or not both the first and the second stimuli are present. If the first and second stimuli are not determined 736 to both be present, the method repeats the determination 736 in the second loop. However, if the first and second stimuli are both determined 736 to be present, the second response is executed 738.

Continuing the second loop, once the second response is executed 738 a determination is made 740 as to whether the first stimulus is still present. It is noted that only the first stimulus is required to be present at step 740, whereas both the first and the second stimuli are required to be present at step 736. If the first stimulus is not determined 740 to be still present, the method returns back to step 736. However, if the first stimulus is determined 740 to still be present, the second response continues to be executed 742.

In sum, the two loops in FIG. 7B are such that when the first stimulus is received the first response is executed until the first stimulus is no longer received; and when the second stimulus is received (assuming the first stimulus is also still being received) the second response is executed until the first stimulus is no longer received.

The arrangement of FIG. 7B may be considered to be, in some sense, "latching" or "sticky". That is, applying the second stimulus is sufficient to prompt execution of the second response, but ceasing to apply the second stimulus does not by itself terminate execution of the second response. Rather, the second stimulus continues until the first stimulus is no longer applied. However, this arrangement is an example only, and other embodiments may be equally suitable.

Such an arrangement might be configured, for example, with a second interaction zone concentric with and inside of a first interaction zone. If the first and second stimuli include passing inside of the first and second interaction zones respectively with an end-effector, then when the end-effector enters the first (outer) interaction zone, the first response is executed, and continues execution so long as the end-effector remains inside the first interaction zone. When the end-effector enters the second (inner) interaction zone, the second response is executed, and continues execution so long as the end-effector remains within the first (outer) interaction zone.

As an example, a first response for such an arrangement could include increasing the brightness of the virtual object, so as to highlight the virtual object to the user; while the second response could include engaging the virtual object with the end-effector. The virtual object would then remain engaged by the end-effector until the user had withdrawn not merely from the second (inner) interaction zone but also from the first (outer) interaction zone.

Thus, interaction zones, stimuli, and/or responses may for some embodiments interact with or depend on one another, being for example asymmetric in operation as shown with regard to FIG. 7A and FIG. 7B.

Figure 8:
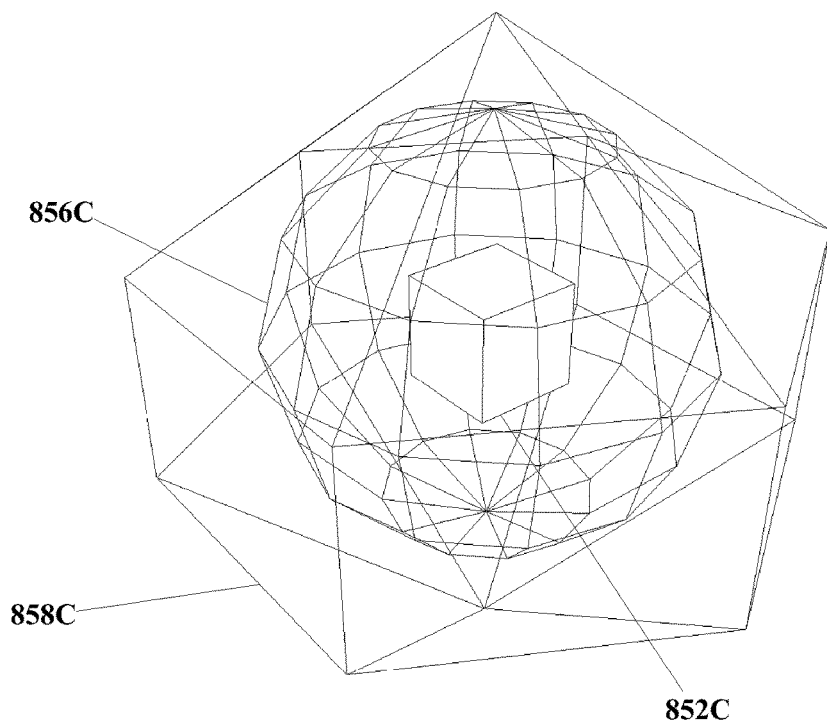
FIG. 8 shows a virtual object in accordance with the present invention, with two interaction zones defined.

Turning for to FIG. 8, as noted previously a single virtual object 852C is not limited to a single interaction zone. FIG. 5 shows an arrangement wherein a first interaction zone 858C and a second interaction zone 856C are both present, the second interaction zone 856C being smaller than and inside of the first interaction zone 858C. The use of multiple interaction zones 856C and 858C for a single virtual object 852C may be suitable for some embodiments of the present invention, since for example it provides a convenient arrangement wherein several different responses to different conditions may be implemented. For example, one response could be generated to a stimulus of the first interaction zone 858C, and another response generated to a stimulus of the second interaction zone 856C. As a more particular example, contact between an end-effector (not shown in FIG. 8) and the larger first interaction zone 858C might cause a response in the form of "waking" the virtual object 852C, causing the virtual object 852C to brighten in color thus making the user aware that the virtual object 852C has been stimulated, while contact between the end-effector and the smaller concentric second interaction zone 856C might activate an application represented by the virtual object 852C.

Although as shown, the first interaction zone 858C is larger than and concentric with the second interaction zone 856C, this is an example only. When multiple interaction zones 856C and 858C are present for a single virtual object 852C, the interaction zones 856C and 858C are not particularly constrained as to their position, size, or other parameters.

Figure 9:
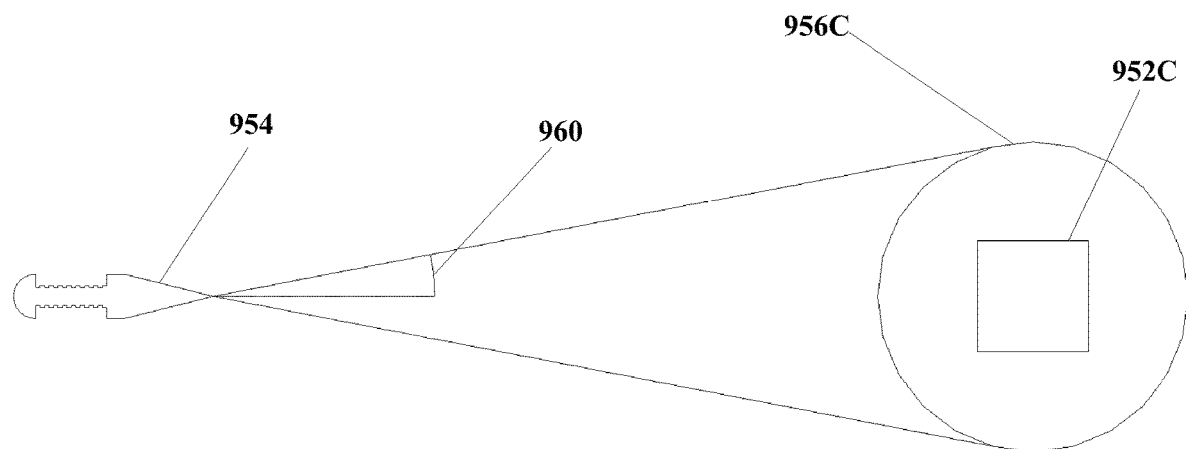
FIG. 9 shows a schematic of a virtual object with an interaction zone in accordance with the present invention defined by an angular dimension.

Moving on to FIG. 9, certain variations in the size, shape, configuration, definition, etc. of the interaction zone have been noted already. However, other variations may also be possible, including but not limited to the following.

As shown in FIG. 9, the interaction zone 956C may be defined so as to vary in size with the distance between the virtual object 952C and some other point, such as an end-effector 954. For example, the interaction zone 956C may be defined so as to have a radial dimension at least equal to the sine of some suitable angle having a vertex at an end-effector 954. In this manner, the apparent size of the interaction zone 956C remains consistent regardless of how close or how far away the virtual object 952 is. A schematic of such an arrangement is shown in FIG. 9, showing an angle 960 defined such that the angle's 960 sine is equal to the radius of an interaction zone 956C. The interaction zone 956C would vary in size depending on the distance between the end-effector 954 and the virtual object 952C, i.e. the interaction zone 956C would become smaller if the virtual object 952C (and the associated interaction zone 956C) came closer to the end-effector 954, and larger if the virtual object 952C moved farther from the end effector 954. Suitable angles would depend on the particulars of a given embodiment, but values in the range of 5 degrees, 2.5 degrees, or 1 degree may be suitable for some embodiments.

It is noted that distance-dependent arrangements do not require the use of an end-effector. For example, a distance-related arrangement might be based on a distance between a user's eye and a virtual object 952C. Other distance-dependent arrangements may also be suitable.

Moreover, insofar as general configuration of the interaction zone is concerned (and not necessarily exclusively referencing a specific illustration herein), although the interaction zone has been described mainly in terms of being a region of space, e.g. an enclosing surface or a volume, this is an example only. Rather than being limited only to geometric definitions, the interaction zone may be thought of more generally as a set of parameters that define whether and in what manner a stimulus may be received. For example, for some embodiments an interaction zone could be defined in terms of a range of headings and/or speeds exhibited by an end-effector. That is, an interaction zone may be defined such that a stimulus is considered to exist if an end-effector moves along a path that is projected to intersect or approach the object for which the interaction zone is defined, and within a given range of speeds.

In such an embodiment, as well as in other suitable embodiments, an interaction zone may exist as a set of rules, with no direct geometric equivalent. It is noted, moreover, that the parameters used to define an interaction zone need not be fixed. An interaction zone may change over time, in response to events (including but not limited to stimulus of the interaction zone itself), in response to system commands, in response to user adjustment, etc.

It is noted that contact between an end-effector and an interaction zone is not necessarily required in order to constitute stimulus; given, for example, the heading-and-speed definition described above for the interaction zone, or other suitable rules-based definitions of the interaction zone, there may be nothing for an end-effector to contact. Moreover, an end-effector is not required for the present invention, so there may be no end-effector to make such contact.

Geometric and non-geometric parameters may be combined for an interaction zone. For example, for some embodiments parameters for an interaction zone could be selected such that stimulus is considered to exist only if en end-effector is both touching/inside a particular region, and also is moving substantially along a particular heading and within a particular range of speeds.

In addition, it is noted that interaction zones are not necessarily limited only to association with virtual objects.

Returning to FIG. 3A through FIG. 3D, the end-effector 354 shown therein does not have an interaction zone. However, although an interaction zone is not illustrated for the end-effector 354, and an interaction zone is not required for the end-effector 354, for certain embodiments an interaction zone could be defined for an end-effector 354. Similarly, it is possible, although not required, to define interaction zones around other physical objects that might be present within the region of a three dimensional interface.

With regard to the stimulus for an interaction zone, a number of arrangements likewise may be suitable. It will be understood that the nature of the type(s) stimulus that may be defined will be to at least some degree a function of the type of interaction zone that is defined, and vice versa.

Again with respect to the arrangement illustrated in FIG. 3A through FIG. 3D, the stimulus is defined as contact between the end-effector 354 and a geometrically defined interaction zone 356C. However, this is an example only. As with the interaction zone 356C itself, events that are defined to serve as stimuli to that interaction zone 356C may be defined geometrically, but stimuli are more generally a set of parameters.

Other parameters besides position of/contact with an end-effector may be suitable for use as stimuli. For example, orientation of an end-effector 354, i.e. what, if anything, the end-effector 354 is pointing at, could be used as a stimulus. In such an arrangement, pointing an end-effector 354 at an interaction zone 356C could constitute a stimulus to that interaction zone 356C. Other potential stimuli include, but are not limited to, speed of an end-effector 354, heading/course of an end-effector 354, gestures and/or patterns of motion of an end-effector 354, multiple contacts by an end-effector 354, dwell time of an end-effector at a particular position 354, etc. Stimulation may be defined so as to require multiple criteria, e.g. pointing an end-effector 354 at a virtual object 352C while the end-effector 354 is within the interaction zone 356C for that virtual object 352C, or approaching the virtual object 352C with the end-effector 354 while the end-effector 354 is within the interaction zone 356C, or disposing the end effector 354 within the interaction zone 356C and keeping it there for some period of time, or moving the end-effector 354 proximate the virtual object 352C while the end-effector 354 is within the interaction zone 356C, etc.

In addition, stimuli are not necessarily limited to the use of an end-effector. For example, a user aligning their eyes so as to have an interaction zone in their central vision, or alternately in their peripheral vision, may be suitable for definition as a stimulus. A range of other user inputs, commands, conditions, etc., including but not limited to keyboard data, system commands, mouse manipulation, voice commands, etc. may be suitable for stimulating an interaction zone of a virtual object.

With regard to the response to the stimulus, a wide range of responses may be suitable. As illustrated in FIG. 3D, the virtual object 352C increases in size in response to the stimulus of the interaction zone 356C. However, this is an example only.

Besides changes in size, other suitable visible changes to the object itself may include changes in shape, color, color saturation, transparency/opacity, position, luminosity, resolution, and focus or apparent focus. The object may move, or if already moving it may change its motion in terms of speed, direction, amplitude, frequency, etc. In addition, the object may be wholly or partially transformed, e.g. becoming animated when it was previously static, becoming three-dimensional when it was two-dimensional, being replaced by an image or video, etc.

Suitable responses are not limited to changes in the virtual object 352C. Although FIG. 3A through FIG. 3D show the virtual object 352C therein changing, the environment around the virtual object 352C may change, and/or the appearance of the three dimensional interface as a whole may change, in response to a stimulus delivered to the interaction zone 356C. Other visible objects or effects may appear, change, and/or disappear within the three dimensional interface in response to the stimulus.

Likewise, responses are not limited only to visible changes. Responses may include audible sounds or changes in existing sounds. Responses may also include features such as vibration, changes in illumination, changes in temperature, etc., e.g. as delivered through a stylus being used as an end-effector, and/or delivered through other devices that are held, worn, or otherwise present.

Responses may also include commands to and/or actions executed within the system(s) being addressed by the three dimensional interface. For example, stimulus delivered with an end-effector to the interaction zone of a virtual object may cause that virtual object to engage with the end-effector, such that the virtual object is then ready to be manipulated, accept commands, receive further stimulus, etc. Responses may also include executing functions associated with the virtual object, such as running a program associated with the virtual object. Responses may include changing a status of a virtual object, for example shifting it between a sleep mode and an active mode. Responses also may include changing the position of the virtual object relative to an end-effector, for example, the virtual object may move towards the end effector, and/or the virtual object may align with the end-effector. In addition or as an alternative, the virtual object may also move with the end-effector. Such arrangements of moving towards, aligning with, and/or moving with an end effector might be referred to collectively as "snapping" the virtual object to the end-effector. Other such responses also may be suitable.

Suitable responses may also include, but are not limited to, changes to the interaction zone that was itself stimulated, and/or changes to other interaction zones of other virtual objects within the three dimensional interface. Such responses may include changes in properties such as the size and/or shape of a geometrically defined interaction zone, and/or may include more extensive changes, e.g. a change from a geometrically defined to a non-geometrically defined interaction zone, the addition or subtraction of interaction zones, etc. Changes may be temporary or permanent.

In addition, a particular stimulus may result in more than one response, delivered in sequence and/or in parallel. For example, a single stimulus may result in an immediate change of color and size of the virtual object, as well as a simultaneous audible sound, and a subsequent vibration.

It is also possible for a single interaction zone to receive two or more stimuli. The criteria that define a particular interaction zone may be such that the interaction zone can receive and distinguish multiple stimuli, in sequence and/or in parallel. Depending on the embodiment, those multiple stimuli may produce a single response, individual responses to individual stimuli (e.g. first and second responses to first and second stimuli), repetitions of a single response, or some other combination.

Figure 10:
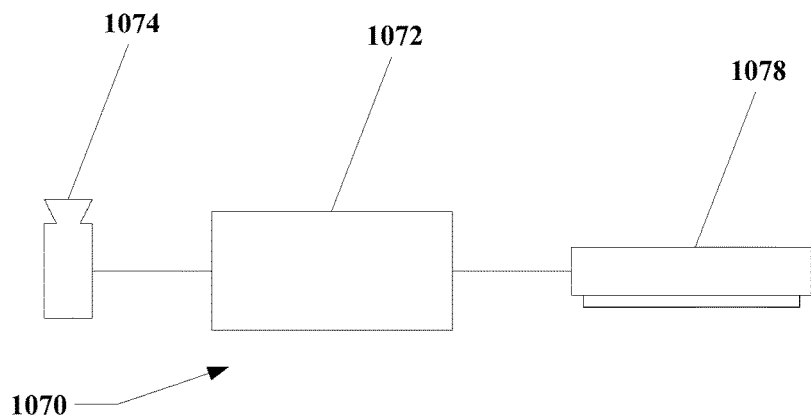
FIG. 10 shows a schematic of an apparatus in accordance with the present invention.

Moving on to FIG. 10, an embodiment of an apparatus 1070 for interacting with a three dimensional interface is shown. The apparatus includes a processor 1072, a sensor 1074 in communication with the processor 1072, and a display 1078 in communication with the processor 1072.

The processor 1072 is adapted to generate a three dimensional interface, to generate at least one virtual object in the three dimensional interface, and to define an interaction zone for the virtual object.

The display 1078 is adapted to output the three dimensional interface and the virtual object, generated by the processor 1072.

The sensor 1074 is adapted to detect a stimulus to the interaction zone of the virtual object.

The processor 1072 is further adapted to generate a response signal when a stimulus is detected by the sensor 1074.

A range of general-purpose, special-purpose, and embedded systems may be suitable for use as the processor 1072. Moreover, it may be equally suitable for the processor 1070 to consist of two or more physical or logical processor components.

A range of devices may be suitable for use as the display 1078, including but not limited to light emitting diodes (LED), organic light emitting diodes (OLED), plasma screen panels (PDP), liquid crystal displays (LCD), etc. Likewise, the use of projected or transmitted displays, where the viewed surface is essentially a passive screen for an image projected or otherwise transmitted after being generated elsewhere, may also be suitable. Other arrangements including but not limited to systems that display images directly onto a user's eyes also may be equally suitable. Either digital or analog display technologies may be suitable.

A range of devices also may be suitable for use as the sensor 1074. As illustrated in FIG. 10, the sensor 1074 is a compact digital camera, adapted to capture images and/or video. A range of cameras, including but not limited to CMOS and CCD cameras, may be suitable. Moreover, sensors other than cameras likewise may be equally suitable, and sensors that capture information other than images and/or video may be equally suitable.

The sensor 1074 is not particularly limited with regard to either what precise event(s) the sensor 1074 may sense in detecting a stimulus to the interaction zone, or how the sensor 1074 may sense the stimulus. For certain embodiments, it may be useful for the sensor 1074 to sense the three dimensional position and/or three dimensional motion of an end-effector as previously described, such as a fingertip, stylus, etc. For example, a sensor 1074 adapted to sense the three dimensional position/motion of such an end-effector could provide position data that would indicate whether the end-effector is touching (e.g. occupying the same position in three dimensional space as) a geometrically defined interaction zone.

The manner by which the processor 1072 is in communication with the display 1074, sensor 1078, and (if present; see below) a response executor is not particularly limited. As illustrated in FIG. 10, components are shown to communicate by wire link, but other arrangements, including but not limited to wireless communication, may be equally suitable.

Likewise, the manner for initiating and/or controlling definition of the interaction zone, determination of stimulus, and execution of a response is not particularly limited. For certain embodiments, it may be useful for a general operating system instantiated on the processor 1072 to initiate and/or control such functions. This may be advantageous, in that it enables the definition of interaction zones around virtual objects without requiring each such virtual object to include capabilities for initiating and/or controlling the interaction zones, stimulus, and response. For example, programs not written to support the use of interaction zones may still have interaction zones defined around virtual objects that are representative of those programs. This may simplify coding, and may help provide backwards compatibility.

However, the use of an operating system in such a way is an example only. It may be equally suitable to initiate and/or control definition of interaction zones, stimuli, and responses through virtual objects themselves, and/or through programs or other constructs associated with the virtual objects, and/or through other approaches.

The apparatus may vary considerably from one embodiment to another, in ways including but not limited to the following.

Figure 11:
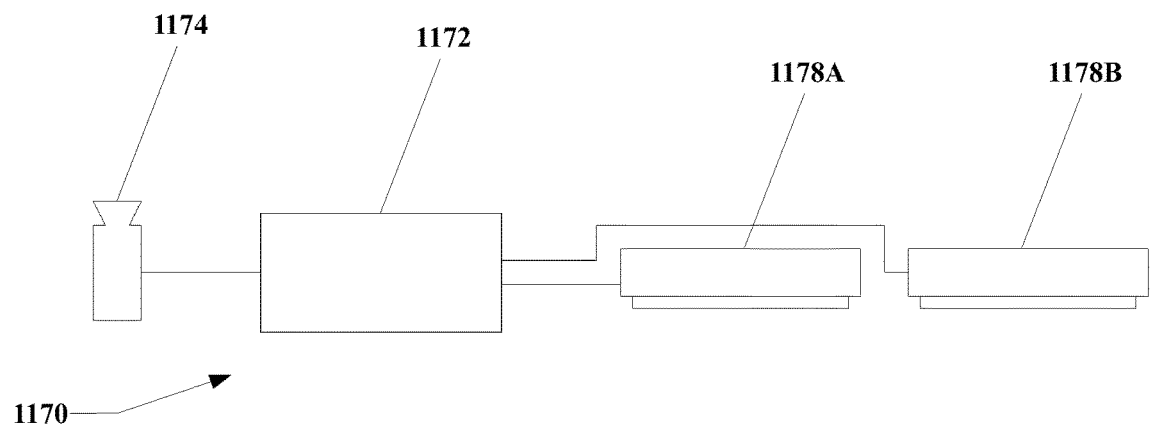
FIG. 11 shows a schematic of an apparatus in accordance with the present invention, with stereo sensors.

FIG. 11 shows an arrangement of an apparatus 1170 wherein the display is a stereo system, with a first display 1178A and a second display 1178B adapted to generate stereo images. The processor is adapted to generate a three dimensional interface and a virtual object, with the first and second displays 1178A and 1178B outputting the three dimensional interface and virtual object. The sensor 1174 is adapted to detect a stimulus to the interaction zone of the virtual object. Such a display arrangement may be useful for some embodiments, as it enables the outputting of three dimensional objects, environments, interfaces, effects, etc., by outputting slightly different images to the first and second displays 1178A and 1178B, comparable to what would be seen by the user's left and right eyes if they were looking at a physical object in three dimensional space. However, the use of a stereo display system is an example only, and other arrangements may be equally suitable.

Figure 12:
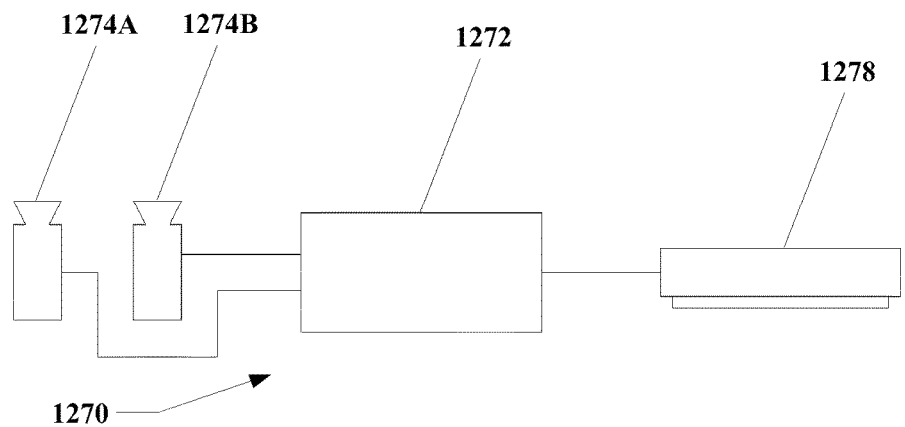
FIG. 12 shows a schematic of an apparatus in accordance with the present invention, with stereo displays.

FIG. 12 shows an embodiment of an apparatus 1270 with a configuration for a sensor that would provide position and/or motion data, using two stereo sensors 1274A and 1274B, arranged so as to capture stereo information of an end-effector. The processor 1272 is adapted to generate a three dimensional interface and a virtual object, with the display 1278 outputting the three dimensional interface and virtual object. This sensor arrangement can be useful, in that it enables stereo three dimensional imaging of the environment. For arrangements that use stereo displays (such as the embodiment shown in FIG. 11), it may also be advantageous in that the general approach to capturing three dimensional data would be comparable to the approach for displaying that data, i.e. stereo capture for stereo display. However, arrangements using stereo sensors 1274A and 1274B are an example only, and other arrangements may be equally suitable.

As previously described, a wide range of response to stimuli may be suitable. Responses that exist entirely within the three dimensional interface, such as changes in the size or other appearance features of a virtual object, may be executed by a processor and outputted by a display. For example, the processor may generate the response signal when the stimulus is communicated to it from the sensor, with the display outputting the result of the response signal. However, as also noted previously, responses other than visual responses may be equally suitable for some embodiments.

Figure 13:
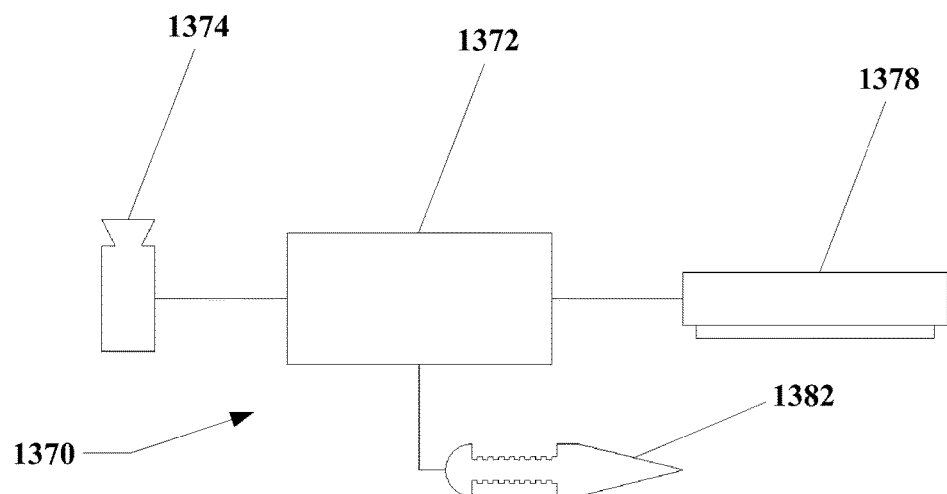
FIG. 13 shows a schematic of an apparatus in accordance with the present invention, with an executor.

FIG. 13 shows an embodiment of an apparatus 1370 that includes a response executor 1382 in communication with the processor 1372, the response executor 1382 being adapted to execute some or all of the response based on a response signal from the processor 1372. The processor 1372 is adapted to generate a three dimensional interface and a virtual object, with the display 1378 outputting the three dimensional interface and virtual object. The sensor 1374 is adapted to detect a stimulus to the interaction zone of the virtual object.

As illustrated in FIG. 13, the response executor 1382 takes the form of a stylus. For example, the stylus could be equipped with lights, vibration generators, heating/cooling systems, etc. and could execute response signals sent by the processor 1372 so as to serve as the response executor 1382. However, this is an example only, and the response executor 1382 is not limited to the form of or incorporation within a stylus, nor is the response executor 1382 otherwise particularly limited with regard to form.

A response executor 1382 can include systems necessary to execute responses that either cannot be or that for some reason are not executed by the display. A response executor 1382 could, for example, include one or more audio speakers adapted to deliver audio responses. Such speakers might be physically incorporated with the processor 1372, display 1374, and/or sensor 1378, e.g. as headphones, earbuds, etc. for a head mounted display, and/or could be freestanding external speakers. However, this is an example only, and other response executors 1382 may be equally suitable. Other response executors 1382 may include, but are not limited to, light sources, vibration generators, systems to generate heat/cold, etc. Response executors 1382 may be incorporated physically with the processor 1372, display 1374, and/or sensor 1378, and/or may be separate and/or freestanding.

Figure 14:
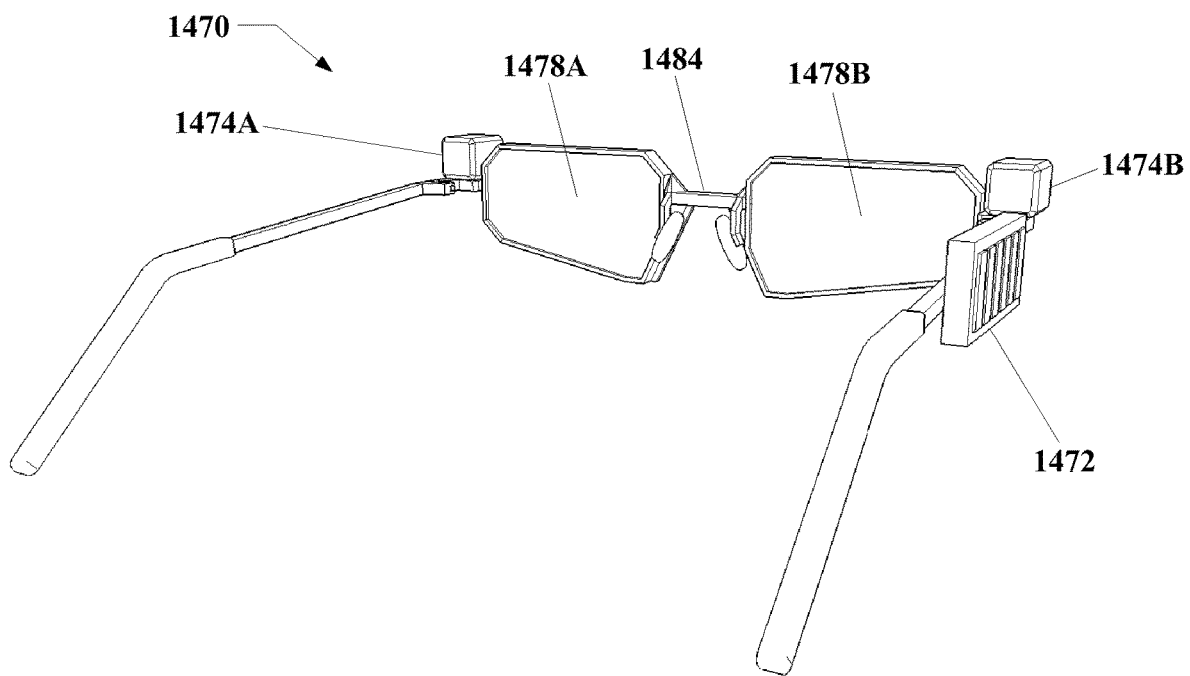
FIG. 14 shows a head mounted display in accordance with the present invention.

The present invention may be incorporated into and/or utilized with a broad range of other devices. For example, FIG. 14 shows an arrangement of an apparatus 1470 in accordance with the present invention as incorporated with a head mounted display. The embodiment shown in FIG. 14 includes with a processor 1472, first and second sensors 1474A and 1474B in a stereo arrangement, and first and second displays 1478A and 1478B also in a stereo arrangement. In addition, the apparatus 1470 includes a body 1484 in the form of a frame for a head mounted display; as shown the body 1484 resembles a pair of glasses, but this is an example only, and other configurations may be equally suitable.

The displays 1478A and 1478B are mounted to the body 1484, with the body 1484 being configured and the displays 1478A and 1478B being mounted such that when a user wears the apparatus 1470, the displays 1478A and 1478B are disposed proximate to and substantially aligned with the user's eyes. Likewise, the sensors 1474A and 1474B mounted to the body 1484 such that when a user wears the apparatus 1470 the field of view of the sensors 1474A and 1474B includes a region in front of the user, e.g. where the user would execute hand motions as input. In the arrangement of FIG. 14, the processor 1472 is also mounted to the body 1484.

However, such an arrangement is presented as an example only, and other embodiments may be equally suitable.

The above specification, examples, and data provide a complete description of the manufacture and use of the composition of the invention. Since many embodiments of the invention can be made without departing from the spirit and scope of the invention, the invention resides in the claims hereinafter appended.

The invention claimed is:

1. A method, comprising:
    generating, by a processing device, an interaction zone associated with a virtual object;
    determining, by the processing device, an uncertainty level of a sensor to identify an input in the interaction zone;
    in response to the uncertainty level of the sensor exceeding a first level, increasing a size of the interaction zone in relation to the virtual object, wherein the increased size of the interaction zone increases a precision level of the sensor in sensing a response associated with the stimulus relative to the virtual object;
    in response to the uncertainty level of the sensor being below a second level, decreasing the size of the interaction zone in relation to the virtual object, wherein the decreases size of the interaction zone decreases the precision level of the sensor in sensing the response associated with the stimulus relative to the virtual object; and
    in response to sensing the input in the interaction zone, executing an instruction associated with the input.

2. The method of claim 1, wherein decreasing the size of the interaction zone further comprises decreasing a sensitivity level of the sensor.

3. The method of claim 1, wherein increasing the size of the interaction zone further comprises increasing a sensitivity level of the sensor.

4. The method of claim 1, further comprising displaying the virtual object in an augmented reality environment with a first space proximate the virtual object and a second space occupied by the virtual object.

5. The method of claim 1, wherein the virtual object occupies at least a portion of the interaction zone.

6. The method of claim 1, wherein the virtual object is entirely encompassed by the interaction zone.

7. The method of claim 1, wherein the interaction zone is visible to the user.

8. The method of claim 1, wherein a size of the interaction zone is defined by a user input.

9. The method of claim 1, wherein at least one of the processing device and/or the sensor is in communication with a wearable device.

10. The method of claim 1, wherein the input comprises a sensed motion generated by a user.

11. The method of claim 1, wherein sensing the input comprises a detection of a user action entering the interaction zone.

12. The method of claim 1, wherein sensing the input comprises a detection of a user action proximate the virtual object.

13. The method of claim 1, wherein executing the instruction further comprises updating a characteristic of the virtual object.

14. A device, comprising:
    a sensor configured to:
        sense a first input within a first defined area proximate a first virtual object; and
        sense a second input within a second defined area proximate a second virtual object distinct from the first virtual object;
    a display configured to:
        display the first virtual object within the first defined area; and
        display the second virtual object within the second defined area;
    a processing device coupled to the sensor and the display, wherein the processing device is configured to:
        determine a first uncertainty level of the sensor to identify the first input in the first defined area;
        in response to the first uncertainty level of the sensor exceeding a first level, increase a size of the first defined area in relation to the first virtual object, wherein the increased size of the first defined area increases a precision level of the sensor for the first defined area;
        in response to the uncertainty level of the sensor being below a second level, decrease the size of the first defined area in relation to the first virtual object, wherein the decreased size of the first defined area decreases the precision level of the sensor for the first defined area;

in response to sensing the first input in the first defined area, execute a first instruction associated with the first input;

determine a second uncertainty level of the sensor to identify the second input in the second defined area;

in response to the second uncertainty level of the sensor exceeding a third level, increase a size of the second defined area in relation to the second virtual object, wherein the increased size of the second defined area increases a precision level of the sensor for the second defined area;

in response to the uncertainty level of the sensor being below a fourth level, decrease the size of the second defined area in relation to the second virtual object, wherein the decreased size of the second defined area decreases the precision level of the sensor for the second defined area; and in response to sensing the second input in the second defined area, execute a second instruction associated with the second input.

15. The device of claim 14, wherein at least one of the first input and the second input comprises a motion detected within a corresponding one of the first defined area or the second defined area.

16. The device of claim 14, wherein at least one of the first input and the second input interacts with a corresponding one of the first virtual object or the second virtual object.

17. An apparatus comprising a processing device configured to:

generate a zone proximate a virtual object;

determine an uncertainly level of a sensor to identify an input within the zone;

in response to the uncertainty level of the sensor exceeding a first level, increase a size of the zone, wherein the increased size of the zone increases a precision level of the sensor; and in response to the uncertainty level of the sensor being below a second level, decrease the size of the zone, wherein the decreased size of the zone decreases the precision level of the sensor; and in response to sensing the input in the interaction zone, executing an instruction associated with the input.

18. The apparatus of claim 17, wherein the input is generated by a user wearing the apparatus in a head mounted device.

* * * * *